United States Patent
Bratz et al.

(10) Patent No.: US 9,538,757 B2
(45) Date of Patent: Jan. 10, 2017

(54) SOLID MIXTURES BASED ON SULFONYLUREAS AND ADJUVANTS

(75) Inventors: Mathias Bratz, Limburgerhof (DE); Karl-Friedrich Jäger, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 537 days.

(21) Appl. No.: 10/043,241

(22) Filed: Jan. 14, 2002

(65) Prior Publication Data

US 2002/0098981 A1   Jul. 25, 2002

Related U.S. Application Data

(63) Continuation of application No. 09/341,524, filed as application No. PCT/EP98/00201 on Jan. 29, 1998, now Pat. No. 6,482,772.

(30) Foreign Application Priority Data

Jan. 30, 1997   (DE) .................................. 197 03 365

(51) Int. Cl.
*A01N 47/36*   (2006.01)

(52) U.S. Cl.
CPC ..................................... *A01N 47/36* (2013.01)

(58) Field of Classification Search
CPC ..................................................... A01N 47/36
USPC ...... 504/367, 311, 211–217; 514/25, 53, 54, 514/211, 212, 358; 536/4.1, 120
See application file for complete search history.

(56) References Cited

U.S. PATENT DOCUMENTS

| 4,547,215 | A |   | 10/1985 | Wolf |   |
|---|---|---|---|---|---|
| H224 | H | * | 3/1987 | Malik et al. | 504/206 |
| 5,258,358 | A | * | 11/1993 | Kocur et al. | 504/205 |
| 5,258,359 | A | * | 11/1993 | Kassebaum et al. | 504/206 |
| 5,385,750 | A |   | 1/1995 | Aleksejczyk et al. | 427/4 |
| 5,550,115 | A | * | 8/1996 | Garst et al. | 514/25 |
| 5,847,146 | A | * | 12/1998 | Schutze et al. | 546/309 |
| 5,888,934 | A | * | 3/1999 | Townson et al. | 504/206 |
| 5,952,285 | A |   | 9/1999 | Hawkins | 510/405 |
| 6,242,382 | B1 | * | 6/2001 | Bratz et al. | 504/133 |
| 6,482,772 | B1 | * | 11/2002 | Bratz et al. | 504/211 |
| 6,559,098 | B1 | * | 5/2003 | Bratz et al. | 504/133 |
| 7,138,360 | B2 | * | 11/2006 | Jager et al. | 504/211 |

FOREIGN PATENT DOCUMENTS

| EP | 220902 |   | 5/1987 |
|---|---|---|---|
| EP | 498 145 |   | 8/1992 |
| EP | 530708 |   | 3/1993 |
| EP | 418175 | * | 3/1999 |
| WO | 95/28410 |   | 10/1995 |
| ZA | 893661 |   | 5/1989 |

OTHER PUBLICATIONS

Kenji Hirai (Herbicide classes in development, mode of actions, targets, genetic engineering and chemistry, Springer-Verlag Berlin Heidelberg New York 2002).*
Nalejewa et al., Weed Tech., 1995, pp. 689-695.
Dunne et al., Weed Sci., 1994, 42, pp. 82-85.
Green, Weed Tech., 1993, 7, pp. 633-640.
DuPont Escort®, Oust®, Telar® Product Information Bulletin, Jun. 1996, 4 pages.
Reagent Chemicals, 6th Ed., Amer. Chem. Soc., 1981, pp. 41, 104.
BASF AG Products: Performance Chemicals, Lutensol® ON web page, 2001.
BASF AG Products: Performance Chemicals; Lutensol® GD web page, 2001.
Hawley's Condensed Chemical Dictionary, 11th Ed., 1987, pp. 433, 1111, 1112, 1235.

* cited by examiner

*Primary Examiner* — Sabiha N Qazi
(74) *Attorney, Agent, or Firm* — Drinker Biddle & Reath LLP

(57) ABSTRACT

Solid mixtures comprising
a) an active compound from the group consisting of the sulfonylureas, and
b) an alkylpolyglucoside.

20 Claims, No Drawings

SOLID MIXTURES BASED ON SULFONYLUREAS AND ADJUVANTS

This is a Continuation Application of application Ser. No. 09/341,524, filed Jul. 13, 1999 now U.S. Pat. No. 6,482,772 (the entire disclosure of which is herewith incorporated by reference), as a national stage of international application No. PCT/EP 98/00201, filed Jan. 29, 1998 (the entire disclosure of which is herewith incorporated by reference).

DESCRIPTION

The present invention relates to solid mixtures based on sulphonylureas and adjuvants.

Sulphonylureas (hereinafter referred to as "SUs") are a group of highly active herbicides which are used widely in crop protection.

Since SUs are taken up through the leaves, SU activity can be improved by adding surfactants such as wetting agents to the spray liquor (cf. Green et al., ANPP, Seizième conference du columa—Journees internationales sur la lutte contre les mauvaises herbes 1995, p. 469-474; "DPX-KG 691—A new surfactant for sulphonyl urea herbicides").

Particularly suitable wetting agents described in the literature are, inter alia, oil adjuvants (Nalejewa et al., Weed Technol. 9 (1995), p. 689-695) or alcohol ethoxylates (see above and Dunne et al., Weed Science 42 (1994), p. 82-85; Green, Weed Technol. 7 (1993), P. 633-640). In agricultural practice, these substances are added by the farmer as tank mix additives to the spray liquor. The mixture of SU herbicide and surfactant is prepared in the spray tank just prior to use.

For example, a double pack is commercially available under the trade name CATO® (Du Pont de Nemours), comprising 25% strength water-dispersible granules of the active compound rimsulfuron (component A) and a wetting agent (component B) which is separately packed and comprises a mixture of 2-butoxyethanol, polyethoxylated tallowamine and nonylphenyl polyethylene glycol ether. For use, the two components are mixed in the spray tank as described above.

In practice, it would be desirable to be able to use ready-to-use formulations already comprising an activity-increasing wetting agent to avoid the problematic mixing immediately prior to use. In this way, it would be possible to avoid logistical problems and mixing mistakes when preparing the spray liquor. Furthermore, solid formulations are generally advantageous from a technical point of view when designing and disposing of the packaging.

It is further known from the literature that SU formulations are problematic with respect to the stability of the active ingredients since, under unfavorable conditions, they may decompose over time with loss of the desired herbicidal activity. The tendency to decompose also causes problems with respect to the registration requirements, since the stability of active crop protection compounds in formulations has to meet certain minimum requirements for registration.

JP-A 62/084004 describes the use of calcium carbonate and sodium tripolyphosphate for stabilizing SU formulations.

JP-A 63/023806 claims to solve the problem by using specific carriers and vegetable oils for preparing solid SU formulations. JP-A 08/104603 describes similar effects when epoxydated natural oils are used. A common feature of these two applications is the incorporation of vegetable oils into the solid formulation to make use of the activity-enhancing properties of these adjuvants, in addition to achieving an improved stability.

Vegetable oils are incorporated into liquid formulations (generally suspension concentrates) to utilize similar effects (cf. EP-A 313317 and EP-A 554015).

It is also known from the prior art to use alkylpolyglucosides as wetting agents/adjuvants.

WO 95/2841 provides solid mixtures of an active compound and an alkylpolyglucoside adsorbed on a carrier.

EP-A 498 154 describes solid formulations of alkylpolyglycosides with the active compound N-phosphonomethylglycine.

It is an object of the present invention to provide SU solid formulations which include the adjuvant from the start and which are superior to the solid formulations of the prior art.

We have found that this object is achieved by solid mixtures comprising
a) a sulfonylurea and
b) an adjuvant from the group of the alkylpolyglycosides.

Surprisingly, it was found that the use of alkylpolyglycosides as wetting agents in SU solid formulations results in a pronounced stabilization of the active ingredient in comparison to other wetting agents (for example ethoxylated fatty amines or alcohol ethoxylates). This effect can be observed especially when water-soluble inorganic salts, such as ammonium sulfate, are present in addition to herbicidally active compounds. The stabilization is especially pronounced when the wetting agent is employed at the concentration required for biological activity.

Storage-stable ready-to-use formulations having good biological activity are obtainable by mixing the SU with other active compounds, alkylpolyglycosides and ammonium sulfate.

The invention further provides processes for preparing the solid mixtures according to the invention and their use as crop protection agents for controlling undesirable harmful plants.

Suitable sulphonylureas a) are generally compounds having the structural unit $$-SO_2NHCN-\underset{|}{\overset{\overset{O}{\|}}{}}$$

Preference is given to SUs of the following structure I:

(I)

$$J-SO_2NHCNR-\underset{}{\overset{\overset{W}{\|}}{}}\begin{pmatrix}X\\N\\\|\\N\end{pmatrix}Z$$

where J is:

J-1

[structure showing benzene ring with H, $R^1$, $R^2$ substituents]

-continued

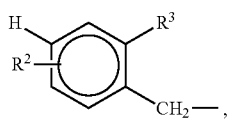

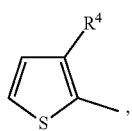

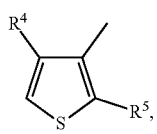

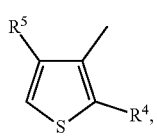

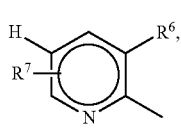

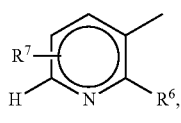

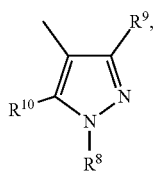

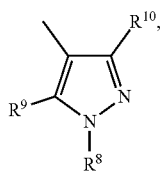

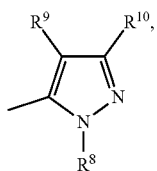

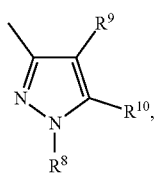

-continued

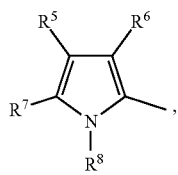

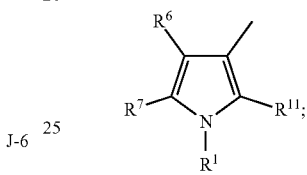

where the substituents R to $R^{18}$ are:

R: H or $CH_3$;

$R^1$: F, Cl, Br, $NO_2$, $C_1$-$C_4$-alkyl, $C_1$-$C_4$-haloalkyl, $C_3$-$C_4$-cycloalkyl, $C_2$-$C_4$-haloalkenyl, $C_1$-$C_4$-alkoxy, $C_1$-$C_4$-haloalkoxy, $C_2$-$C_4$-alkoxyalkoxy, $CO_2R^{12}$, $C(O)NR^{13}R^{14}$, $SO_2NR^{15}R^{16}$, $S(O)_nR^{17}$, $C(O)R^{18}$, $CH_2CN$ or L;

$R^2$: H, F, Cl, Br, CN, $CH_3$, $OCH_3$, $SCH_3$, $CF_3$ or $OCF_2H$;

$R^3$: Cl, $NO_2$, $CO_2CH_3$, $CO_2CH_2CH_3$, $SO_2N(CH_3)_2$, $SO_2CH_3$, $SO_2CH_2CH_3$, $OCH_3$, or $OCH_2CH_3$;

$R^4$: $C_1$-$C_3$-alkyl, $C_1$-$C_4$-haloalkyl, $C_1$-$C_4$-alkoxy, $C_2$-$C_4$-haloalkenyl, F, Cl, Br, $NO_2$, $CO_2R^{12}$, $C(O)NR^{13}R^{14}$, $SO_2NR^{15}R^{16}$, $S(O)_nR^{17}$, $C(O)R^{18}$ or L;

$R^5$: H, F, Cl, Br or $CH_3$;

$R^6$: $C_1$-$C_4$-alkyl, $C_1$-$C_4$-alkoxy, $C_2$-$C_4$-haloalkenyl, F, Cl, Br, $CO_2R^{12}$, $C(O)NR^{13}R^{14}$, $SO_2NR^{15}R^{16}$, $S(O)_nR^{17}$, $C(O)R^{18}$ or L;

$R^7$: H, F, Cl, $CH_3$ or $CF_3$;

$R^8$: H, $C_1$-$C_4$-alkyl or pyridyl;

$R^9$: $C_1$-$C_4$-alkyl, $C_1$-$C_4$-alkoxy, F, Cl, Br, $NO_2$, $CO_2R^{12}$, $SO_2NR^{15}R^{16}$, $S(O)_nR^{17}$, $OCF_2H$, $C(O)R^{18}$, $C_2$-$C_4$-haloalkenyl or L;

$R^{10}$: H, Cl, F, Br, $C_1$-$C_4$-alkyl or $C_1$-$C_4$-alkoxy;

$R^{11}$: H, $C_1$-$C_4$-alkyl, $C_1$-$C_4$-alkoxy, haloalkenyl, F, Cl, Br, $CO_2R^{12}$, $C(O)NR^{13}R^{14}$, $SO_2NR^{15}R^{16}$, $S(O)_nR^{17}$, $C(O)R^{18}$ or L;

$R^{12}$: $C_1$-$C_4$-alkyl, with or without substitution by halogen, $C_1$-$C_4$-alkoxy or CN, allyl or propargyl;

$R^{13}$: H, $C_1$-$C_4$-alkyl or $C_1$-$C_4$-alkoxy;

$R^{14}$: $C_1$-$C_4$-alkyl;

$R^{15}$: H, $C_1$-$C_4$-alkoxy, $C_1$-$C_4$-alkoxy, allyl or cyclopropyl;

$R^{16}$: H or $C_1$-$C_4$-alkyl;

$R^{17}$: $C_1$-$C_4$-alkyl, $C_1$-$C_4$-haloalkyl, allyl or propargyl;

$R^{18}$: $C_1$-$C_4$-alkyl, $C_1$-$C_4$-haloalkyl or $C_3$-$C_5$-cycloalkyl, with or without substitution by halogen;

n is 0, 1 or 2;

L has the structure II

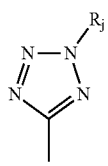

(II)

where $R_j$: H or $C_1$-$C_3$-alkyl;

W: O or S;

X: H, $C_1$-$C_4$-alkyl, $C_1$-$C_4$-alkoxy, $C_1$-$C_4$-haloalkoxy, $C_1$-$C_4$-haloalkyl, $C_1$-$C_4$-haloalkylthio, $C_1$-$C_4$-alkylthio, halogen, $C_2$-$C_5$-alkoxyalkyl, $C_2$-$C_5$-alkoxyalkoxy, amino, $C_1$-$C_3$-alkylamino or di($C_1$-$C_3$-alkyl)amino;

Y: H, $C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio, $C_2$-$C_5$-alkoxyalkyl, $C_2$-$C_5$-alkoxyalkoxy, amino, $C_1$-$C_3$-alkylamino, di($C_1$-$C_3$-alkyl)amino, $C_3$-$C_4$-alkenyloxy, $C_3$-$C_4$-alkanyloxy, $C_2$-$C_5$-alkylthioalkyl, $C_2$-$C_5$-alkylsulfinylalkyl, $C_2$-$C_5$-alkylsulfonylalkyl, $C_2$-$C_4$-alkenyl, $C_3$-$C_5$-cycloalkyl, azido, fluorine or cyano;

Z: CH or N;

and agriculturally useful salts thereof.

Below, some suitable SUs are listed by their INN (International Nonproprietary Name) according to the Pesticide Manual:

ACC 322140;

Amidosulfuron;

Azimsulfuron (N-[[(4,6-dimethoxy-2-pyrimidinyl)amino]carbonyl]-1-methyl-4-(2-methyl-2H-tetrazol-5-yl)-1H-pyrazole-5-sulfonamide);

Bensulfuron-methyl (methyl 2-[[[[[(4,6-dimethoxy-2-pyrimidinyl)-amino]carbonyl]amino]sulfonyl]methyl]benzoate);

Ethyl 2-[[[[(4-chloro-6-methoxy-2-pyrimidinyl)amino]carbonyl]-amino]sulfonyl]benzoate (chlorimuron ethyl);

2-Chloro-N-[[(4-methoxy-6-methyl-1,3,5-triazin-2-yl)amino]carbonyl]benzenesulfonamide (chlorsulfuron);

Chlorsulfoxim;

Cinosulfuron;

Cyclosulfamuron;

Ethametsulfuron-methyl (methyl 2-[[[[[4-ethoxy-6-(methylamino)-1,3,5-triazin-2-yl]amino]carbonyl]amino]sulfonyl]benzoate);

Ethoxysulfuron;

Flazasulfuron;

Flupyrsulfuron (methyl 2-[[[[(4,6-dimethoxy-2-pyrimidinyl)-amino]carbonyl]amino]sulfonyl]-6-(trifluoromethyl)-3-pyridine-carboxylate);

Halosulfuron-methyl;

Imazosulfuron;

Methyl 2-[[[[(4-methoxy-6-methyl-1,3,5-triazin-2-yl)amino]-carbonyl]amino]sulfonyl]benzoate (metsulfuron methyl);

nicosulfuron (2-[[[[(4,6-dimethoxy-2-pyrimidinyl)amino]carbonyl]-amino]sulfonyl]-N,N-dimethyl-3-pyridinecarboxamide);

Oxasulfuron;

Primisulfuron (methyl 2-[[[[[4,6-bis(difluoromethoxy)-2-pyrimidinyl]amino]carbonyl]amino]sulfonyl]benzoate);

Prosulfuron;

Pyrazosulfuron-ethyl (ethyl 5-[[[[(4,6-dimethoxy-2-pyrimidinyl)amino]carbonyl]amino]sulfonyl]-1-methyl-1H-pyrazole-4-carboxylate);

Rimsulfuron (N-[[(4,6-dimethoxy-2-pyrimidinylamino]-carbonyl]-3-(ethylsulfonyl)-2-pyridinesulfonamide);

Sulfosulfuron;

Sulfometuron-methyl (methyl 2-[[[[(4,6-dimethyl-2-pyrimidinyl)-amino]carbonyl]amino]sulfonyl]benzoate);

Thifensulfuron-methyl (methyl-3-[[[[(4-methoxy-6-methyl-1,3,5-triazin-2-yl)amino]carbonyl]amino]sulfonyl]-2-thiophenecarboxylate);

2-(2-Chloroethoxy)-N-[[(4-methoxy-6-methyl-1,3,5-triazin-2-yl)amino]carbonyl]benzenelsulfonamide (triasulfuron);

Tribenuron-methyl (methyl 2-[[[[N-(4-methoxy-6-methyl-1,3,5-triazin-2-yl)-N-methylamino]carbonyl]amino]sulfonyl]benzoate);

and

Triflusulfuron-methyl (methyl 2-[[[[[4-(dimethylamino)-6-(2,2,2-trifluoroethoxy)-1,3,5-triazin-2-yl]amino]carbonyl]amino]sulfonyl]-3-methylbenzoate).

Particular preference is given to sulfonylureas of the formula III (equivalent to the formula I where $J=J_1$) as known, for example, from EP-A 388 873, EP-A 559 814, EP-A 291 851 and EP-A 446 743:

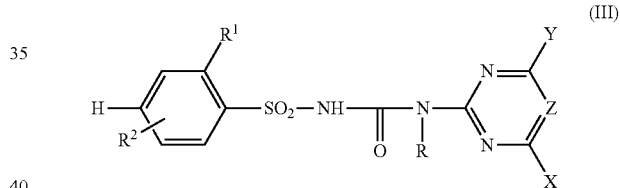

(III)

where:

$R^1$ is $C_1$-$C_4$-alkyl, which may carry from one to five of the following groups: methoxy, ethoxy, $SO_2CH_3$, cyano, chlorine, fluorine, $SCH_3$, $S(O)CH_3$;

halogen;

a group $ER^{19}$, in which E is O, S or $NR^{20}$;

$COOR^{12}$;

$NO_2$;

$S(O)_nR^{17}$, $SO_2NR^{15}R^{16}$, $CONR^{13}R^{14}$;

$R^2$ is hydrogen, methyl, halogen, methoxy, nitro, cyano, trifluoromethyl, trifluoromethoxy, difluoromethoxy or methylthio;

Y is F, $CF_3$, $CF_2Cl$, $CF_2H$, $OCF_3$, $OCF_2Cl$, $C_1$-$C_4$-alkyl or $C_1$-$C_4$-alkoxy;

X is $C_1$-$C_2$-alkoxy, $C_1$-$C_2$-alkyl, $C_1$-$C_2$-alkylthio, $C_1$-$C_2$-alkylamino, di-$C_1$-$C_2$-alkylamino, halogen, $C_1$-$C_2$-haloalkyl, $C_1$-$C_2$-haloalkoxy, R is hydrogen or methyl;

$R^{19}$ is $C_1$-$C_4$-alkyl, $C_2$-$C_4$-alkenyl, $C_2$-$C_4$-alkynyl or $C_3$-$C_6$-cycloalkyl, each of which may carry from 1 to 5 halogen atoms; furthermore, in the case that E is O or $NR^{20}$, $R^{19}$ is also methylsulfonyl, ethylsulfonyl, trifluoromethylsulfonyl, allylsulfonyl, propargylsulfonyl or dimethylsulfamoyl;

$R^{20}$ is hydrogen, methyl or ethyl;
$R^{12}$ is a $C_1$-$C_4$-alkyl group which may carry up to three of the following radicals: halogen, $C_1$-$C_4$-alkoxy, allyl or propargyl;
$R^{13}$ is H, $C_1$-$C_4$-alkyl or $C_1$-$C_4$-alkoxy;
$R^{14}$ is $C_1$-$C_4$-alkyl;
$R^{17}$ is a $C_1$-$C_4$-alkyl group which may carry from one to three of the following radicals: halogen, $C_1$-$C_4$-alkoxy, allyl or propargyl;
$R^{15}$ is hydrogen, a $C_1$-$C_2$-alkoxy group or a $C_1$-$C_4$-alkyl group;
$R^{16}$ is hydrogen or a $C_1$-$C_4$-alkyl group,
n is 1 or 2,
Z is N, CH.

Particularly preferred sulfonylureas of the formula III are those of the general formula I where J is $J_1$ and the remaining substituents have the following meanings:
$R^1$ is $CO_2CH_3$, $CO_2C_2H_5$, $CO_2iC_3H_7$, $CF_3$, $CF_2H$, $OSO_2CH_3$, $OSO_2N(CH_3)_2$, Cl, $NO_2$, $SO_2N(CH_3)_2$, $SO_2CH_3$ or $N(CH_3)SO_2CH_3$,
$R^2$ is hydrogen, Cl, F or $C_1$-$C_2$-alkyl,
Y is $CF_2H$, $OCF_3$, $OCF_2Cl$, $CF_2Cl$, $CF_3$ or F
X is $OCH_3$, $OC_2H_5$, $OCF_3$, $OCF_2Cl$; $CF_3$, Cl, F, $NH(CH_3)$, $N(CH_3)_2$ or $C_1$-$C_2$-alkyl,
R is hydrogen, and
Z is N or CH.

Very particular preference is given to those compounds of the formula III which are listed in the table below.

TABLE

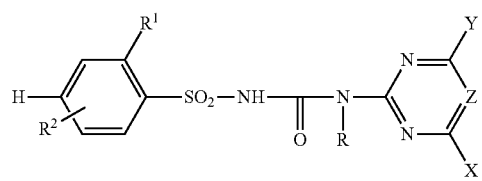

(III)

| No. | $R^1$ | $R^2$ | R | Y | X | Z |
|---|---|---|---|---|---|---|
| 1 | $CO_2CH_3$ | H | H | $OCF_2Cl$ | $OCH_3$ | CH |
| 2 | $CO_2C_2H_5$ | H | H | $OCF_2Cl$ | $OCH_3$ | CH |
| 3 | $CO_2iC_3H_7$ | H | H | $OCF_2Cl$ | $OCH_3$ | CH |
| 4 | $NO_2$ | H | H | $OCF_2Cl$ | $OCH_3$ | CH |
| 5 | $SO_2CH_3$ | H | H | $OCF_2Cl$ | $OCH_3$ | CH |
| 6 | $SO_2N(CH_3)_2$ | H | H | $OCF_2Cl$ | $OCH_3$ | CH |
| 7 | Cl | H | H | $OCF_2Cl$ | $OCH_3$ | CH |
| 8 | $N(CH_3)SO_2CH_3$ | H | H | $OCF_2Cl$ | $OCH_3$ | CH |
| 9 | $OSO_2CH_3$ | H | H | $OCF_2Cl$ | $OCH_3$ | CH |
| 10 | $OSO_2N(CH_3)_2$ | H | H | $OCF_2Cl$ | $OCH_3$ | CH |
| 11 | $CF_3$ | H | H | $OCF_2Cl$ | $OCH3$ | CH |
| 12 | $CF_2H$ | H | H | $OCF_2Cl$ | $OCH_3$ | CH |
| 13 | $CO_2CH_3$ | H | H | $OCF_3$ | $OCH_3$ | CH |
| 14 | $CO_2C_2H_5$ | H | H | $OCF_3$ | $OCH_3$ | CH |
| 15 | $CO_2iC_3H_7$ | H | H | $OCF_3$ | $OCH_3$ | CH |
| 16 | $NO_2$ | H | H | $OCF_3$ | $OCH_3$ | CH |
| 17 | $SO_2CH_3$ | H | H | $OCF_3$ | $OCH_3$ | CH |
| 18 | $SO_2N(CH_3)_2$ | H | H | $OCF_3$ | $OCH_3$ | CH |
| 19 | Cl | H | H | $OCF_3$ | $OCH_3$ | CH |
| 20 | $N(CH_3)SO_2CH_3$ | H | H | $OCF_3$ | $OCH_3$ | CH |
| 21 | $OSO_2CH_3$ | H | H | $OCF_3$ | $OCH_3$ | CH |
| 22 | $OSO_2N(CH_3)_2$ | B | H | $OCF_3$ | $OCH_3$ | CH |
| 23 | $CF_3$ | H | H | $OCF_3$ | $OCH_3$ | CH |
| 24 | $CF_2H$ | H | H | $OCF_3$ | $OCH_3$ | CH |
| 25 | $CO_2CH_3$ | H | H | F | $OCH_3$ | CH |
| 26 | $CO_2C_2H_5$ | H | H | F | $OCH_3$ | CH |
| 27 | $CO_2iC_3H_7$ | H | H | F | $OCH_3$ | CH |
| 28 | $NO_2$ | H | H | F | $OCH_3$ | CH |
| 29 | $SO_2CH_3$ | H | H | F | $OCH_3$ | CH |
| 30 | $SO_2N(CH_3)_2$ | H | H | F | $OCH_3$ | CH |
| 31 | Cl | H | H | F | $OCH_3$ | CH |

TABLE-continued

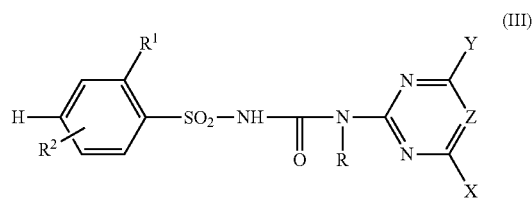

(III)

| No. | $R^1$ | $R^2$ | R | Y | X | Z |
|---|---|---|---|---|---|---|
| 32 | $N(CH_3)SO_2CH_3$ | H | H | F | $OCH_3$ | CH |
| 33 | $OSO_2CH_3$ | H | H | F | $OCH_3$ | CH |
| 34 | $OSO_2N(CH_3)_2$ | H | H | F | $OCH_3$ | CH |
| 35 | $CF_3$ | H | H | F | $OCH_3$ | CH |
| 36 | $CF_2H$ | H | H | F | $OCH_3$ | CH |
| 37 | $CO_2CH_3$ | H | H | $CF_3$ | $OCH_3$ | N |
| 38 | $CO_2C_2H_5$ | H | H | $CF_3$ | $OCH_3$ | N |
| 39 | $CO_2iC_3H_7$ | H | H | $CF_3$ | $OCH_3$ | N |
| 40 | $NO_2$ | H | H | $CF_3$ | $OCH_3$ | N |
| 41 | $SO_2CH_3$ | H | H | $CF_3$ | $OCH_3$ | N |
| 42 | $SO_2N(CH_3)_2$ | H | H | $CF_3$ | $OCH_3$ | N |
| 43 | Cl | H | H | $CF_3$ | $OCH_3$ | N |
| 44 | $N(CH_3)SO_2CH_3$ | H | H | $CF_3$ | $OCH_3$ | N |
| 45 | $OSO_2CH_3$ | H | H | $CF_3$ | $OCH_3$ | N |
| 46 | $OSO_2N(CH_3)_2$ | H | H | $CF_3$ | $OCH_3$ | N |
| 47 | $CF_3$ | H | H | $CF_3$ | $OCH_3$ | N |
| 48 | $CF_2H$ | H | H | $CF_3$ | $OCH_3$ | N |
| 49 | $CO_2CH_3$ | H | H | $CF_3$ | $OCH_3$ | CH |
| 50 | $CO_2C_2H_5$ | H | H | $CF_3$ | $OCH_3$ | CH |
| 51 | $CO_2iC_3H_7$ | H | H | $CF_3$ | $OCH_3$ | CH |
| 52 | $NO_2$ | H | H | $CF_3$ | $OCH_3$ | CH |
| 53 | $SO_2CH_3$ | H | H | $CF_3$ | $OCH_3$ | CH |
| 54 | $SO_2N(CH_3)_2$ | H | H | $CF_3$ | $OCH_3$ | CH |
| 55 | Cl | H | H | $CF_3$ | $OCH_3$ | CH |
| 56 | $N(CH_3)SO_2CH_3$ | H | H | $CF_3$ | $OCH_3$ | CH |
| 57 | $OSO_2CH_3$ | H | H | $CF_3$ | $OCH_3$ | CH |
| 58 | $OSO_2N(CH_3)_2$ | H | H | $CF_3$ | $OCH_3$ | CH |
| 59 | $CF_3$ | H | H | $CF_3$ | $OCH_3$ | CH |
| 60 | $CF_2H$ | H | H | $CF_3$ | $OCH_3$ | CH |
| 61 | $CO_2CH_3$ | H | H | $CF_2H$ | $OCH_3$ | N |
| 62 | $CO_2C_2H_5$ | H | H | $CF_2H$ | $OCH_3$ | N |
| 63 | $CO_2iC_3H_7$ | H | H | $CF_2H$ | $OCH_3$ | N |
| 64 | $NO_2$ | H | H | $CF_2H$ | $OCH_3$ | N |
| 65 | $SO_2CH_3$ | H | H | $CF_2H$ | $OCH_3$ | N |
| 66 | $SO_2N(CH_3)_2$ | H | H | $CF_2H$ | $OCH_3$ | N |
| 67 | Cl | H | H | $CF_2H$ | $OCH_3$ | N |
| 68 | $N(CH_3)SO_2CH_3$ | H | H | $CF_2H$ | $OCH_3$ | N |
| 69 | $OSO_2CH_3$ | H | H | $CF_2H$ | $OCH_3$ | N |
| 70 | $OSO_2N(CH_3)_2$ | H | H | $CF_2H$ | $OCH_3$ | N |
| 71 | $CF_3$ | H | H | $CF_2H$ | $OCH_3$ | N |
| 72 | $CF_2H$ | H | H | $CF_2H$ | $OCH_3$ | N |
| 73 | $CO_2CH_3$ | H | H | $CF_2H$ | $OCH_3$ | CH |
| 74 | $CO_2C_2H_5$ | H | H | $CF_2H$ | $OCH_3$ | CH |
| 75 | $CO_2iC_3H_7$ | H | H | $CF_2H$ | $OCH_3$ | CH |
| 76 | $NO_2$ | H | H | $CF_2H$ | $OCH_3$ | CH |
| 77 | $SO_2CH_3$ | H | H | $CF_2H$ | $OCH_3$ | CH |
| 78 | $SO_2N(CH_3)_2$ | H | H | $CF_2H$ | $OCH_3$ | CH |
| 79 | Cl | H | H | $CF_2H$ | $OCH_3$ | CH |
| 80 | $N(CH_3)SO_2CH_3$ | H | H | $CF_2H$ | $OCH_3$ | CH |
| 81 | $OSO_2CH_3$ | H | H | $CF_2H$ | $OCH_3$ | CH |
| 82 | $OSO_2N(CH_3)_2$ | H | H | $CF_2H$ | $OCH_3$ | CH |
| 83 | $CF_3$ | H | H | $CF_2H$ | $OCH_3$ | CH |
| 84 | $CF_2H$ | H | H | $CF_2H$ | $OCH_3$ | CH |
| 85 | $CO_2CH_3$ | H | H | $CF_2Cl$ | $OCH_3$ | N |
| 86 | $CO_2C_2H_5$ | H | H | $CF_2Cl$ | $OCH_3$ | N |
| 87 | $CO_2iC_3H_7$ | H | H | $CF_2Cl$ | $OCH_3$ | N |
| 88 | $NO_2$ | H | H | $CF_2Cl$ | $OCH_3$ | N |
| 89 | $SO_2CH_3$ | H | H | $CF_2Cl$ | $OCH_3$ | N |
| 90 | $SO_2N(CH_3)_2$ | H | H | $CF_2Cl$ | $OCH_3$ | N |
| 91 | Cl | H | H | $CF_2Cl$ | $OCH_3$ | N |
| 92 | $N(CH_3)SO_2CH_3$ | H | H | $CF_2Cl$ | $OCH_3$ | N |
| 93 | $OSO_2CH_3$ | H | H | $CF_2Cl$ | $OCH_3$ | N |
| 94 | $OSO_2N(CH_3)_2$ | H | H | $CF_2Cl$ | $OCH_3$ | N |
| 95 | $CF_3$ | H | H | $CF_2Cl$ | $OCH_3$ | N |
| 96 | $CF_2H$ | H | H | $CF_2Cl$ | $OCH_3$ | N |
| 97 | $CO_2CH_3$ | 3-F | H | Cl | $OCH_3$ | CH |
| 98 | $CF_2CF_3$ | H | H | $CH_3$ | $OCH_3$ | N |

TABLE-continued

(III)

| No. | R¹ | R² | R | Y | X | Z |
|---|---|---|---|---|---|---|
| 99 | $CF_2CF_3$ | H | H | $CH_3$ | $OCH_3$ | N |
| 100 | $SO_2C_2H_5$ | H | H | F | $OCH_3$ | CH |

Of course, component a) may also be a mixture of more than one sulfonylureas.

Component b) of the solid formulations according to the invention comprises one or more alkylpolyglycosides (referred to as APG below). Depending on the chemical structure and on the way the synthesis is carried out, the substance class of the APGs is referred to in the literature as alkylglucosides, alkylglycosides, alkylpolyglucosides or alkylpolyglycosides.

Herewithin below, only the term APG will be used in lieu of all the other names, always referring to the entire group of the abovementioned compounds.

Especialy preferred components b) are APGs having a mean degree of polymerization in the range from 1.0 to 6.0. They can be characterized by the formula II $$R^{21}O(Z)_a$$

where $R^{21}$ is an alkyl radical having from 4 to 30, preferably from 8 to 18, carbon atoms and Z is a glycoside radical having from 5 to 6 carbon atoms and a is a value in the range from 1 to 6, or from 1 to 3, or from 1 to 2, and preferably from 1.0 to 1.7. Corresponding products are commercially available, inter alia under the names Agrimul® PG, APG®, Plantaren® or Glucopon® (all by Henkel), Lutensol® (BASF), Atplus® (ICI Surfactants) or Triton® (Union Carbide).

Specific examples are:
Agrimul® PG 2067: an APG having a $C_8$-$C_{10}$-alkyl group and an average degree of polymerization of 1.7;
APG® 425: an APG having a $C_8$-$C_{16}$-alkyl group and an average degree of polymerization of 1.6;
APG® 625: an APG having a $C_{12}$-$C_{16}$-alkyl group and an average degree of polymerization of 1.6;
APG® 300: an APG having a $C_8$-$C_{16}$-alkyl group and an average degree of polymerization of 1.4;
AG 6202: an APG having a 2-ethylhexyl chain (Akzo Nobel) and an average degree of polymerization of 1.6;
Lutensol®GD 70: an APG having a $C_{10}$-$C_{12}$-alkyl group (BASF AG) and an average degree of polymerization of 1.3;
Agrimul® PG 2069: an APG having a $C_9$-$C_{11}$-alkyl group and an average degree of polymerization of 1.6;
Glucopon® 600: an APG having a $C_{12}$-$C_{16}$-alkyl group and an average degree of polymerization of 1.4;
Plantaren® 1300: an APG having a $C_{12}$-$C_{16}$-alkyl group and an average degree of polymerization of 1.6.

Other preferred APGs are Atplus® 258, Atplus® 264, Atplus® 430, Atplus® 460, Atplus® 469 and Atplus® 450 (alkyl polysaccharide/adjuvant blends, ICI Surfactants) and to Agrimul® PG 215, Agrimul® PG 600, Triton® BG-10 and Triton® CG-110.

Rather than unbranched alkyl radicals, particular preference may be given to branched alkyl radicals.

The percentage of the component a) in the solid mixtures according to the invention is generally in the range from 0.5 to 75% by weight, preferably from 1 to 25% by weight, based on the total weight of the formulation.

The percentage of the APGs (component b)) is generally in the range from 1 to 75, in particular from 1 to 50, especially from 5 to 25, % by weight, based on the total weight of the formulation.

In addition to the components a) and b), the solid mixtures according to the invention may comprise further active compounds which are miscible with sulfonylureas and/or produce synergistic effects. The corresponding products are known to the person skilled in the art and are described in the literature. The following groups of other active compounds are listed as examples under their INNs:
c1: 1,3,4-thiadiazoles:
buthidazole, cyprazole;
c2: amides:
allidochlor (CDAA), benzoylprop-ethyl, bromobutide, chlorthiamid, dimepiperate, dimethenamid, diphenamid, etobenzanid (benzchlomet), flamprop-methyl, fosamin, isoxaben, monalide, naptalame, pronamid (propyzamid), propanil;
c3: aminophosphoric acids:
bilanafos (bialaphos), buminafos, glufosinate-ammonium, glyphosate, sulfosate;
c4: aminotriazoles:
amitrol;
c5: anilides:
anilofos, mefenacet, thiafluamide;
c6: aryloxyalkanoic acids:
2,4-D, 2,4-DB, clomeprop, dichlorprop, dichlorprop-P, (2,4-DP-P), fenoprop (2,4,5-TP), fluoroxypyr, MCPA, MCPB, mecoprop, mecoprop-P, napropamide, napropanilide, triclopyr;
c7: benzoic acids:
chloramben, dicamba;
c8: benzothiadiazinones:
Bentazon;
c9: bleachers:
clomazone (dimethazone), diflufenican, fluorochloridone, flupoxam, fluridone, pyrazolate, sulcotrione (chlor-mesulone) isoxaflutol, 2-(2'-chloro-3'-ethoxy-4'-ethylsulfonylbenzoyl)-4-methylcyclohexane-1,3-dione;
c10: carbamates:
asulam, barban, butylate, carbetamide, chlorbufam, chlorpropham, cycloate, desmedipham, diallate, EPTC, esprocarb, molinate, orbencarb, pebulate, phenisopham, phenmedipham, propham, prosulfocarb, pyributicarb, sulfallate (CDEC), terbucarb, thiobencarb (benthiocarb), tiocarbazil, triallate, vernolate;
c11: quinolinic acids:
quinclorac, quinmerac;
c12: chloroacetanilides:
acetochlor, alachlor, butachlor, butenachlor, diethatyl ethyl, dimethachlor, dimethenamide (cf. also under category c2), metazachlor, metolachlor, pretilachlor, propachlor, prynachlor, terbuchlor, thenylchlor, xylachlor;
c13: cyclohexenones:
alloxydim, caloxydim, clethodim, cloproxydim, cycloxydim, sethoxydim, tralkoxydim, 2-{1-[2-(4-chloro-phenoxy)propyloxyimino]butyl}-3-hydroxy-5-(2H-tetrahydrothiopyran-3-yl)-2-cyclohexen-1-one;
c14: dichloropropionic acids:
dalapon;
c15: dihydrobenzofuranes:
ethofumesate;

c16: dihydrofuran-1-ones:
flurtamone;
c17: dinitroanilines:
benefin, butralin, dinitramin, ethalfluralin, fluchloralin, isopropalin, nitralin, oryzalin, pendimethalin, prodiamine, profluralin, trifluralin;
c18: dinitrophenoles:
bromofenoxim, dinoseb, dinoseb-acetat, dinoterb, DNOC;
c19: diphenyl ethers:
acifluorfen-sodium, aclonifen, bifenox, chlornitrofen (CNP), difenoxuron, ethoxyfen, fluorodifen, fluoroglycofen-ethyl, fomesafen, furyloxyfen, lactofen, nitrofen, nitrofluorfen, oxyfluorfen;
c20: bipyridyliums:
cyperquat, difenzoquat-methylsulfat, diquat, paraquat-dichlorid;
c21: ureas:
benzthiazuron, buturon, chlorbromuron, chloroxuron, chlortoluron, cumyluron, dibenzyluron, cycluron, dimefuron, diuron, dymron, ethidimuron, fenuron, fluormeturon, isoproturon, isouron, karbutilat, linuron, methabenzthiazuron, metobenzuron, metoxuron, monolinuron, monuron, neburon, siduron, tebuthiuron, trimeturon;
c22: imidazoles:
iscarbamide;
c23: imidazolinones:
imazamethapyr, imazapyr, imazaquin, imazethabenz-methyl (imazame), imazethapyr, imazamox;
c24: oxadiazoles:
methazole, oxadiargyl, oxadiazone;
c25: oxiranes:
tridiphane
c26: phenols:
bromoxynil, ioxynil;
c27: phenoxypropionic esters:
clodinafop, cyhalofop-butyl, diclofop-methyl, fenoxaprop-ethyl, fenoxaprop-p-ethyl, fenthiapropethyl, fluazifop-butyl, fluazifopp-butyl, haloxyfop-ethoxyethyl, haloxyfop-methyl, haloxyfop-p-methyl, isoxapyrifop, propaquizafop, quizalofop-ethyl, quizalofop-p-ethyl, quizalofoptefuryl;
c28: phenylacetic acids:
chlorfenac (fenac);
c29: phenylpropionic acids:
chlorophenprop-methyl;
c30: protoporphyrinogene IX oxydase inhibitors:
benzofenap, cinidon-ethyl, flumiclorac-pentyl, flumioxazin, flumipropyn, flupropacil, fluthiacet-methyl, pyrazoxyfen, sulfentrazone, thidiazimine, carfentrazone, azafenidin;
c31: pyrazoles:
nipyraclofen;
c32: pyridazines:
chloridazon, maleic hydrazide, norflurazon, pyridate;
c33: pyridinecarboxylic acids:
clopyralid, dithippyr, picloram, thaizopyr;
c34: pyrimidyl ethers:
pyrithiobac-acid, pyrithiobac-sodium, pyriminobac-methyl, bispyribenzoxim, bispyribac-sodium;
c35: sulfonamides:
flumetsulam, metosulam, cloransulam-methyl, diclosulam;
c36: triazines:
ametryn, atrazin, aziprotryn, cyanazine, cyprazine, desmetryn, dimethamethryn, dipropetryn, eglinazin-ethyl, hexazinon, procyazine, prometon, prometryn, propazin, secbumeton, simazin, simetryn, terbumeton, terbutryn, terbutylazin, trietazin, dimesyflam;
c37: triazinones:
ethiozin, metamitron, metribuzin;
c38: triazolecarboxamides:
triazofenamid;
c39: uracils:
bromacil, lenacil, terbacil;
c40: various:
benazolin, benfuresate, bensulide, benzofluor, butamifos, cafenstrole, chlorthal-dimethyl (DCPA), cinmethylin, dichlobenil, endothall, fluorbentranil, mefluidide, perfluidone, piperophos, diflufenzopyr, diflufenzopyr-sodium or the environmentally compatible salts of the abovementioned groups of active compounds.

Other, preferred active compounds c) are, for example, bromobutide, dimethenamide, isoxaben, propanil, glufosinate-ammonium, glyphosate, sulfosate,
mefenacet, thiafluamide,
2,4-D, 2,4-DB, dichlorprop, dichlorprop-P,
dichlorprop-P(2,4-DP-P), fluoroxopyr, MCPA, mecoprop, mecoprop-P, dicamba,
bentazon,
clomazone, diflufenican, sulcotrione, isoxaflutole, phenmedipham, thiobencarb,
quinclorac, quinmerac,
acetochlor, alachlor, butachlor, metazachlor, metolachlor, pretilachlor,
butroxydim, caloxydim, clethodim, cycloxydim, sethoxydim, tralkoxydim, 2-{1-[2-(4-chlorophenoxy) propyloxyimino]butyl}-3-hydroxy-5-(2H-tetrahydrothiopyran-3-yl)-2-cyclohexen-1-one, pendimethalin,
acifluorfen-sodium, bifenox, fluoroglycofen-ethyl, fomesafen, lactofen,
chlortoluron, cycluron, dymron, isoproturon, metabenzthiazuron, imazaquin, imazamox, imazethabenz-methyl, imazethapyr, bromoxynil, ioxynil,
clodinafop, cyhlaofop-butyl, fenoxyprop-ethyl, fenoxaprop-p-ethyl, haloxyfop-p-methyl,
cinidon-ethyl, flumiclorac-pentyl, carfentrazone, flumipropyn, fluthiacet-methyl,
pyridate,
clopyralid,
bispyribac-sodium, pyriminobac-methyl,
flumetsulam, metosulam,
atrazin, cyanazine, terbutylazine,
benazolin, benfuresate, cafenstrole, cinemthylin, ammonium-bentazon, cloquintocet, diflufenzopyr, diflufenzopyr-sodium, pyraflufen-ethyl.

Particular preference is given to the following compounds c):
2,4-D, dichlorprop-P, MCPA, mecoprop-P,
dicamba,
bentazon,
diflufenican, sulcotrione,
quinclorac,
caloxydim, cycloxydim, sethoxydim, 2-{1-[2-(4-chlorophenoxy)propyloxyimino]butyl}-3-hydroxy-5-(2H-tetrahydrothiopyran-3-yl)-2-cyclohexen-1-one,
acifluorfen-sodium, fluoroglycofen-ethyl,
bromoxynil,
fenoxyprop-ethyl,
cinidon-ethyl,
atrazin, terbutylazin,
ammonium-bentazon, cloquintocet,
thiafluamid, isoxaflutole, diflufenzopyr, diflufenzopyr-Na, carfentrazone, imazamox.

Very particular preference is given to the following compounds c):
2,4-D, dichlorprop-P, mecoprop-P, MCPA, ammonium-bentazon, bentazon, diflufenican, quinclorac, 2-{1-[2-(4-chlorophenoxy)propyloxyimino]butyl}-3-hydroxy-5-(2H-tetrahydrothiopyran-3-yl)-2-cyclohexen-1-one, caloxydim, cycloxydim, sethoxydim, fluoroglycofen-ethyl, cinidon-ethyl, atrazin, terbutylazine, dicamba, diflufenzopyr and diflufenzopyr-Na.

The percentage of the other active compounds c), if present, is generally in the range from 0.5 to 75, preferably from 1 to 60, % by weight of the formulation.

In addition to the components a), b) and c) described above, the solid mixtures according to the invention may also contain customary formulation auxiliaries.

Suitable surfactants are the alkali metal salts, alkaline earth metal salts and ammonium salts of aromatic sulfonic acids, for example ligno-, phenol-, naphthalene- and dibutylnaphthalenesulfonic acid, and of fatty acids of arylsulfonates, of alkyl ethers, of lauryl ethers, of fatty alcohol sulfates and of fatty alcohol glycol ether sulfates, condensation products of sulfonated naphthalene and its derivatives with formaldehyde, condensation products of naphthalene or of the naphthalenesulfonic acids with phenol and formaldehyde, condensation products of phenol or of phenolsulfonic acid with formaldehyde, condensation products of phenol with formaldehyde and sodium sulfite, polyoxyethylene octylphenyl ethers, ethoxylated isooctyl-, octyl- or nonylphenol, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated triarylphenols, salts of phosphorylated triarylphenolethoxylates, polyoxypropylene alkyl ethers, lauryl alcohol polyglycol ether acetate, sorbitol esters, lignin-sulfite liquors or methylcellulose or mixtures thereof.

The percentage of any surfactants used is generally in the range from 0.5 to 25% by weight, based on the total weight of the solid mixture.

The solid mixtures according to the invention may also be used together with carriers. Examples of carriers include: mineral earths such as silicas, silica gels, silicates, talc, kaolin, attaclay, limestone, chalk, loess, clay, dolomite, diatomaceous earth, calcium sulfate, magnesium sulfate, magnesium oxide, ground synthetic materials, fertilizers such as ammonium sulfate, ammonium phosphate, ammonium nitrate, thiourea and urea, products of vegetable origin such as cereal meal, tree bark meal, wood meal and nutshell meal, cellulose powders, attapulgites, montmorillonites, mica, vermiculites, synthetic silicas and synthetic calcium silicates or mixtures thereof.

Further additives which may be used in customary amounts are:
water-soluble compounds or salts, such as:
sodium sulfate, potassium sulfate, sodium chloride, potassium chloride, sodium acetate, ammonium hydrogen sulfate, ammonium chloride, ammonium acetate, ammonium formate, ammonium oxalate, ammonium carbonate, ammonium hydrogen carbonate, ammonium thiosulfate, ammonium hydrogen diphosphate, ammonium dihydrogen monophosphate, ammonium sodium hydrogen phosphate, ammonium thiocyanate, ammonium sulfamate or ammonium carbamate;
binders, such as:
polyvinylpyrrolidone, polyvinyl alcohol, partially hydrolyzed polyvinyl acetate, carboxymethylcellulose, starch, vinylpyrolidone/vinyl acetate copolymers and polyvinyl acetate or mixtures thereof;
lubricants, such as:
Mg stearate, Na stearate, talc or polyethylene glycol or mixtures thereof;

defoamers, such as:
silicone emulsions, long-chain alcohols, phosphoric esters, acetylene diols, fatty acids or organofluorine compounds, and
complex formers, such as:
salts of ethylenediaminetetraacetic acid (EDTA), salts of trinitrilotriacetic acids or salts of polyphosphoric acids or mixtures thereof.

The solid mixtures according to the invention can be prepared in the form of powders, granules, briquettes, tablets and similar formulation variants. In addition to powders, particular preference is given to granules. The powders can be water-soluble or water-dispersible powders. The granules can be water-soluble or water-dispersible granules for use in spray application or granules for spreading for direct application. The mean particle size of the granules is generally between 200 μm and 2 mm.

The resulting granule formulations are dust-free, free flowing, non-caking products which dissolve or disperse readily in cold water.

Owing to their properties, the products can easily be packaged in relatively large amounts. In addition to packages such as sacks or bags made of plastic, paper or laminated material, they can be handled in cardboard boxes or other bulk containers. To further reduce the exposure of the user, it is possible to package the products in water-soluble film-bags, such as, for example, polyvinyl alcohol film-bags, which can be placed directly into the spray tank, where they dissolve. Suitable water-soluble films are, inter alia, polyvinyl alcohol or cellulose derivatives, such as methylcellulose, methylhydroxypropylcellulose or carboxymethylcellulose. By portioning the product into quantities suitable for use, the user no longer comes into contact with the product. The water-soluble bags are preferably packaged in a water-vapor-impermeable outer wrapper, such as polyethylene film, polyethylene-laminated paper or aluminum foil.

The solid formulations according to the invention can be prepared by various processes known to the person skilled in the art.

Preferred preparation processes for the mentioned formulations are extruder granulation, spray drying, fluidized-bed agglomeration, mixer granulation and disk granulation.

Fluidized-bed granulation is particularly suitable. Depending on the desired composition of the formulation, an aqueous solution, emulsion or suspension containing all the ingredients of the recipe is sprayed into a fluidized-bed granulator and agglomerated.

If desired, it is also possible to initially introduce active compound salts and/or inorganic ammonium salts into the granulator and to spray them with a solution or emulsion/suspension of the remaining ingredients of the recipe to agglomerate them. Furthermore, it is possible to apply aqueous solutions, emulsions or suspensions containing specific ingredients of the recipe in succession to granules of the active compound, to an active compound salt and/or to an inorganic ammonium salt to obtain different coating layers.

In general, the granules are dried sufficiently during the fluidized-bed granulation. However, it may be advantageous to carry out a separate drying step in the same or in a separate drier after the granulation. Following the granulation/drying, the product is cooled and sieved.

A further particularly suitable process is extruder granulation. Extruder granulation is preferably carried out using a cage extruder, radial extruder or dome extruder with minimum compaction of the granulated pellets.

For granulation, a mixture of solids is premixed in a suitable mixer with a granulation liquid until an extrudable material is obtained. This is then extruded in one of the above-mentioned extruders. For extrusion, hole sizes from 0.3 to 3 mm are used (preferably 0.5-1.5 mm). Suitable mixtures of solids are mixtures of active compounds, formulation auxiliaries and, if appropriate, water-soluble salts. In general, these are preground. Sometimes it is sufficient to pregrind only the water-insoluble substances in suitable mills.

Suitable granulation liquids are water, the APGs according to the invention or aqueous solutions thereof. Aqueous solutions of inorganic salts, nonionic surfactants, anionic surfactants, solutions of binders such as polyvinylpyrrolidone, polyvinyl alcohol, carboxymethylcellulose, starch, vinylpyrrolidine/vinylacetate copolymers, sugars, dextrin or polyethylene glycol. After extruder granulation, the resulting granules are dried and, if required, sieved to remove particles which are too coarse or too fine.

COMPARATIVE EXAMPLE 1

A pre-mix comprising:

| | |
|---|---|
| 73.1% g | of SU 1 (compound No. 47 from Table 1) (technical grade, 95.7%) |
| 8% g | of Tamol ® NH |
| 17.9% g | of Ufoxane ® 3A | was mixed and ground in a high-speed rotary mill.

| | |
|---|---|
| 7.1 g | of pre-mix 1 |
| 5 g | of Extrusil ® (Degussa) |
| 77.9 g | of ammonium sulfate | were mixed in a Moulinette household blender with 29 g of Lutensol® ON 80 as a 50% strength aqueous solution. The resulting material was extruded using an extruder (KAR-75, Fitzpatrick Europe). The resulting moist granules were dried in a drying cabinet.

COMPARATIVE EXAMPLE 2

A pre-mix comprising:

| | |
|---|---|
| 73.1% g | of SU 1 (technical grade, 95.7%) |
| 8% g | of Tamol ® NH |
| 17.9% g | of Ufoxane ® 3A | was mixed and ground in a high-speed rotary mill.

| | |
|---|---|
| 7.1 g | of pre-mix |
| 15 g | of Extrusil ® (Degussa) |
| 77.9 g | of ammonium sulfate | were mixed in a Moulinette household blender with 23 g of Armoblem® 557 as a 50% strength aqueous solution. The resulting material was extruded using an extruder (KAR-75, Fitzpatrick Europe). The resulting moist granules were dried in a drying cabinet.

COMPARATIVE EXAMPLE 3

A pre-mix comprising:

| | |
|---|---|
| 285 g | of distilled water |
| 30.3 g | of SU 1 (technical grade) |
| 20 g | of Ufoxane ® 3A |
| 10 g | of Tamol ® NH |
| 2.5 g | of anti-foam emulsion SRE |
| 30 g | of Sipernat ® 50 |
| 560 g | of Pluronic ® PE 6400 | was mixed and bead-milled. The resulting suspension was used later as spray mix.

137 g of pulverulent ammonium sulfate were charged initially to a laboratory fluidized-bed granulator (Combi Coata®, Niro Aeromatic). A two-material nozzle was situated above the fluidized bed. The initial charge was fluidized with air of 120° C. inlet temperature. The spray pressure of the two-material nozzle was adjusted to 2 bar. The spray mix was sprayed into the fluidized bed and the water was evaporated. The resulting granules were sieved through a sieve having a mesh width of 0.2 mm to remove any fine particles.

COMPARATIVE EXAMPLE 4

A mixture comprising:

| | |
|---|---|
| 6.9 g | of metsulfuron-methyl (technical grade, 99%) |
| 3 g | of Tamol ® NH |
| 6 g | of Ufoxane ® 3A |
| 15 g | of Extrusil ® |
| 43.1 g | of ammonium sulfate | was mixed intensively and ground using a laboratory high-speed rotary mill. The resulting powder mixture was mixed with 25 parts of Lutensol® ON 30 in a planetary mixer (Kenwood Chef). The resulting material was extruded using an extruder (DGL-1, Fitzpatrick Europe). The resulting moist granules were dried in a fluidized-bed dryer.

EXAMPLE 1

A pre-mix comprising:

| | |
|---|---|
| 73.1% g | of SU 1 (technical grade, 95.7%) |
| 8% g | of Tamol ® NH |
| 17.9% g | of Ufoxane ® 3A | was mixed and ground in a high-speed rotary mill.

| | |
|---|---|
| 7.1 g | of pre-mix |
| 15 g | of Extrusil ® (Degussa) |
| 52.9 g | of ammonium sulfate |
| 18.5 g | of Lutensol ® GD 70 | were mixed in a Moulinette household blender. The resulting material was extruded using an extruder (KAR-75, Fitzpatrick Europe). The resulting moist granules were dried in a drying cabinet.

EXAMPLE 2

A pre-mix comprising:

| | |
|---|---|
| 285 g | of distilled water |
| 15.8 g | of SU 1 (technical grade) |
| 31 g | of Ufoxane ® 3A |
| 15.3 g | of Tamol ® NH |
| 2.5 g | of anti-foam emulsion SRE |
| 7.5 g | of Sipernat ® 22 |
| 75 g | of AG ® 6202 | was mixed and bead-milled. The resulting suspension was used later as spray mix.

120 g of pulverulent ammonium sulfate were charged initially to a laboratory fluidized-bed granulator (Combi Coata®, Niro Aeromatic). A two-material nozzle was situated above the fluidized bed. The initial charge was fluidized with air of 120° C. inlet temperature. The spray pressure of the two-material nozzle was adjusted to 2 bar. The spray mix was sprayed into the fluidized bed and the water was evaporated. The resulting granules were sieved through a sieve having a mesh width of 0.2 mm to remove any fine particles.

EXAMPLE 3

A pre-mix comprising:

| | |
|---|---|
| 73.1% g | of SU 1 (technical grade, 95.7%) |
| 8% g | of Tamol ® NH |
| 17.9% g | of Ufoxane ® 3A | was mixed and ground in a high-speed rotary mill.

| | |
|---|---|
| 7.1 g | of pre-mix |
| 15 g | of Extrusil ® (Degussa) |
| 52.9 g | of aminonium sulfate |
| 16 g | of AG ® 6202 | were mixed in a Moulinette household blender. The resulting material was extruded using an extruder (KAR-75, Fitzpatrick Europe). The resulting moist granules were dried in a drying cabinet.

EXAMPLE 4

A mixture comprising:

| | |
|---|---|
| 5.1 g | of SU 1 (technical grade, 98.54%) |
| 3 g | of Tamol ® NH |
| 6 g | of Ufoxane ® 3A |
| 15 g | of Extrusil ® (Degussa) |
| 44.9 g | of ammononium sulfate | was mixed and ground in a high-speed rotary mill. The resulting powder was mixed with 21 g of Atplus® 450 and 1 g of anti-foam agent SRE in a Moulinette household blender. The resulting material was extruded using an extruder (KAR-75, Fitzpatrick Europe). The resulting moist granules were dried in a drying cabinet.

EXAMPLE 5

A mixture comprising:

| | |
|---|---|
| 5.1 g | of SU 1 (technical grade, 98.54%) |
| 3 g | of Tamol ® NH |
| 6 g | of Ufoxane ® 3A |
| 15 g | of Extrusil ® (Degussa) |
| 44.9 g | of ammonium sulfate | was mixed and ground in a high-speed rotary mill. The resulting powder was mixed with 25 g of Agrimul® PG 2067 and 1 g of anti-foam agent SRE in a Moulinette household blender. The resulting material was extruded using an extruder (KAR-75, Fitzpatrick Europe). The resulting moist granules were dried in a drying cabinet.

EXAMPLE 6

A pre-mix comprising:

| | |
|---|---|
| 5.1 g | of SU 1 (technical grade, 98.5%) |
| 3.1 g | of cinidon-ethyl (technical grade, 98%) |
| 1 g | of Tamol ® NH |
| 2 g | of Ufoxane ® 3A |
| 15 g | of Extrusil ® (Degussa) |
| 47.8 g | of ammonium sulfate | was mixed and ground in a jet mill.

| | |
|---|---|
| 74 g | of pre-mix |
| 25 g | of Lutensol ® GD 70 (alkylpolyglucoside, BASF AG, technical grade, 70%) |
| 1 g | of anti-foam agent SRE | were mixed in a planetary mixer (Kenwood Chef) and admixed with a total of 4 g of water (based on 100 g of product). The resulting material was extruded using an extruder (DGL-1, Fitzpatrick Europe). The resulting moist granules were dried in a fluidized-bed dryer. This gave readily dispersible granules.

EXAMPLE 7

A pre-mix comprising:

| | |
|---|---|
| 5.1 g | of SU 1 (technical grade, 98.5%) |
| 3.1 g | of cinidon-ethyl (technical grade, 98%) |
| 1 g | of Tamol ® NH |
| 2 g | of Ufoxane ® 3A |
| 15 g | of Extrusil ® (Degussa) |
| 47.8 g | of ammonium sulfate | was mixed and ground in a jet mill.

| | |
|---|---|
| 74 g | of pre-mix |
| 22.5 g | of AG ® 6202 (alkylpolyglucoside, Akzo, technical grade, 65%) |
| 1 g | of anti-foam agent SRE | were mixed in a planetary mixer (Kenwood Chef). The resulting material was extruded using an extruder (DGL-1, Fitzpatrick Europe). The resulting moist granules were dried in a fluidized-bed dryer. This gave readily dispersible granules.

EXAMPLE 8

A mixture comprising:

| | |
|---|---|
| 126 g | of cinidon-ethyl |
| 209 g | of SU 1 |
| 4361 g | of distilled water |
| 359 g | of Ufoxane ® 3A |
| 2153 g | of Tamol ® NH |
| 34 g | of anti-foam emulsion SRE |
| 1538 g | of AG ® 6202 | was mixed and bead-milled. The resulting suspension was used as spray mix. The spray mix was injected into a laboratory fluidized-bed granulator (MP1®, Niro Aeromatic) and dried to give water-dispersible granules. The temperature of the air used for drying was 120° C. and the two-material nozzle, which was situated above the fluidized bed, was operated with a spray pressure of 2 bar. The resulting granules were sieved through a sieve having a mesh width of 0.2 mm to remove any fine particles.

EXAMPLE 9

A pre-mix comprising:

| | |
|---|---|
| 73.1 g | of SU 1 (technical grade, 95.7%) |
| 8 g | of Tamol ® NH |
| 17.9 g | of Ufoxane ® 3A | was mixed and ground in a high-speed rotary mill.

| | |
|---|---|
| 3.8 g | of pre-mix |
| 60.6 g | of bentazon-Na (technical grade, 87.5%) |
| 22.6 g | of ammonium sulfate |
| 2 g | of Lutensol ® GD 70 (alkylpolyglucoside, BASF AG, technical grade, 70%) |
| 1% g | of anti-foam agent SRE | were mixed in a planetary mixer (Kenwood Chef) and admixed with a total of 9 g of water (based on 100 g of product). The resulting material was extruded using an extruder (DGL-1, Fitzpatrick Europe). The resulting moist granules were dried in a fluidized-bed dryer.

EXAMPLE 10

A pre-mix comprising:

| | |
|---|---|
| 71 g | of SU 1 (technical grade, 98.5%) |
| 8 g | of Tamol ® NH |
| 21 g | of Ufoxane ® 3A | was mixed and ground in a high-speed rotary mill.

| | |
|---|---|
| 3.8 g | of pre-mix |
| 55.7 g | of ammonium-bentazon (technical grade, 95.2%) |
| 26.5 g | of ammonium sulfate |
| 12 g | of Lutensol ® GD 70 (alkylpolyglucoside, BASF AG, technical grade, 70%) |
| 1 g | of anti-foam agent SRE | were mixed in a planetary mixer (Kenwood Chef) and admixed with a total of 9 g of water (based on 100 g of product). The resulting material was extruded using an extruder (DGL-1, Fitzpatrick Europe). The resulting moist granules were dried in a fluidized-bed dryer.

EXAMPLE 11

A pre-mix comprising:

| | |
|---|---|
| 1173 g | of distilled water |
| 92 g | of SU 1 (technical grade) |
| 125 g | of Ufoxane ® 3A |
| 110 g | of ammonium sulfate |
| 375 g | of AG ® 6202 |
| 250 g | of Extrusil ® | was mixed and bead-milled. The resulting suspension was then used as spray mix. 1523 g of sodium bentazon having a particle size of less than 1.0 mm were charged initially to a laboratory fluidized-bed granulator (MP1®, Niro Aeromatic). A two-material nozzle was situated above the fluidized bed. The initial charge was fluidized with air of 120° C. inlet temperature. The spray pressure of the two-material nozzle was adjusted to 2 bar. The spray mix was sprayed into the fluidized bed and the water was evaporated. The resulting granules were sieved through a sieve having a mesh width of 0.2 mm to remove any fine particles.

EXAMPLE 12

A pre-mix comprising:

| | |
|---|---|
| 2548 g | of distilled water |
| 75 g | of SU 1 |
| 228 g | of Ufoxane ® 3A |
| 730 g | of Tamol ® NH |
| 451 g | of AG ® 6202 |
| 301 g | of Extrusil ® | was mixed and bead-milled. The resulting suspension was then used as spray mix.

1065 g of finely powdered magnesium-mecoprop-P were charged initially to a laboratory fluidized-bed granulator (MP1®, Niro Aeromatic). A two-material nozzle was situated above the fluidized bed. The initial charge was fluidized with air of 120° C. inlet temperature. The spray pressure of the two-material nozzle was adjusted to 2.5 bar. The spray mix was sprayed into the fluidized bed and the water was evaporated. The resulting granules were sieved through a sieve having a mesh width of 0.2 mm to remove any fine particles.

EXAMPLE 13

A pre-mix comprising:

| | |
|---|---|
| 2655 g | of distilled water |
| 800 g | of AG ® 6202 |
| 420 g | of Ufoxane ® 3A |
| 210 g | of Tamol ® NH |
| 340 g | of Sipernat ® 50 S | was mixed and bead-milled. The resulting suspension was used as spray liquid A.

1020 g of pulverulent ammonium sulfate were charged initially to a laboratory fluidized-bed granulator (MP1®, Niro Aeromatic). A two-material nozzle was situated above the fluidized bed. The initial charge was fluidized with air of 120° C. inlet temperature. The spray pressure of the two-material nozzle was adjusted to 2 bar. The spray mix was sprayed into the fluidized bed and the water was evaporated. This gave the pre-granules A.

A further pre-mix B comprising:

| | |
|---|---|
| 1725 g | of distilled water |
| 103 g | of SU 1 (technical grade) |
| 618 g | of MCPA |
| 127 g | of aqueous sodium hydroxide solution |
| 192 g | of Ufoxane ® 3A |
| 96 g | of Tamol ® NH |
| 12.6 g | of anti-foam emulsion SRE | was mixed and used as spray liquid B.

1875 g of pre-granules A were charged initially to a laboratory fluidized-bed granulator (MP1®, Niro Aeromatic). A two-material nozzle was situated above the fluidized bed. The initial charge was fluidized with air of 120° C. inlet temperature. The spray pressure of the two-material nozzle was adjusted to 2 bar. The spray mix B was sprayed into the fluidized bed and the water was evaporated. The resulting granules were sieved through a sieve having a mesh width of 0.2 mm to remove any fine particles.

EXAMPLE 14

A pre-mix comprising:

| | |
|---|---|
| 6 g | of SU 1 |
| 10 g | of clefoxydim-lithium |
| 10 g | of Extrusil ® |
| 10 g | of urea |
| 3 g | of Morwet ® EFW |
| 1 g | of Aerosol ® OT B |
| 40 g | of Tamol ® NH | was mixed intensively and ground using an air jet mill. The resulting powder mixture was mixed with 20 parts of AG® 6202 in a planetary mixer (Kenwood Chef). Furthermore, to produce an extrudable material, 1.8% of water were added. The resulting material was extruded using an extruder (DGL-1, Fitzpatrick Europe). The resulting moist granules were dried in a fluidized-bed dryer.

EXAMPLE 15

A mixture comprising:

| | |
|---|---|
| 6.9 g | of metsulfuron-methyl (technical grade, 99%) |
| 3 g | of Taxnol ® NH |
| 6 g | of Ufoxane ® 3A |
| 15 g | of Extrusil ® |
| 43.1 g | of ammonium sulfate | was mixed intensively and ground using a laboratory high-speed rotary mill. The resulting powder mixture was mixed with 25 parts of AG® 6202 in a planetary mixer (Kenwood Chef). The resulting material was extruded using an extruder (DGL-1, Fitzpatrick Europe). The resulting moist granules were dried in a fluidized-bed dryer.

EXAMPLE 16

A mixture comprising:

| | |
|---|---|
| 6.9 g | of metsulfuron-methyl (technical grade, 99%) |
| 3 g | of Tamol ® NH |
| 6 g | of Ufoxane ® 3A |
| 15 g | of Extrusil ® |
| 43.1 g | of ammonium sulfate | was mixed intensively and ground using a laboratory high-speed rotary mill. The resulting powder mixture was mixed with 25 parts of Lutensol® GD 70 in a planetary mixer (Kenwood Chef). The resulting material was extruded using an extruder (DGL-1, Fitzpatrick Europe). The resulting moist granules were dried in a fluidized-bed dryer.

EXAMPLE 17

A pre-mix comprising:

| | |
|---|---|
| 423 g | of distilled water |
| 17.7 g | of aqueous sodium hydroxide solution |
| 93.2 g | of dicamba (technical grade) |
| 15.2 g | of SU 1 (technical grade) |
| 39.8 g | of Ufoxane ® 3A |
| 79.5 g | of Tamol ® NH |
| 92.3 g | of AG ® 6202 (as 65% strength aqueous solution) | were mixed in the stated order and then used as spray mixture.

The granulation was carried out in a laboratory fluidized-bed granulator (Combi Coata®, Niro Aeromatic). A two-material nozzle was situated above the fluidized bed. Fluidization was performed with air of 120° C. inlet temperature. The spray pressure of the two-material nozzle was adjusted to 2 bar. The spray mix was sprayed into the fluidized bed and the water was evaporated. The resulting granules were sieved through a sieve having a mesh width of 0.2 mm to remove any fine particles.

EXAMPLE 18

A pre-mix comprising:

| |
|---|
| 1350 g of distilled water |
| 178 g of SU 1 (technical grade) |
| 173 g of Ufoxane$^R$ 3A |
| 346 g of Tamol$^R$ NH |
| 1077 g of AG$^R$ 6202 (as 65% strength aqueous solution) |
| 15 g of anti-foam emulsion SRE | was mixed and bead-milled. The resulting suspension was used as spray liquid A.

A further pre-mix comprising:

| |
|---|
| 1325 g of distilled water |
| 145 g of aqueous sodium hydroxide solution |
| 781 g of dicamba (technical grade) | was mixed until dissolved and used as spray liquid B.

In a laboratory fluidized-bed granulator (MP1, Niro Aeromatic), 900 g of pulverulent ammonium sulfate were initially charged. A two-material nozzle was situated above the fluidized bed. The initial charge was fluidized with air of 120° C. inlet temperature. The spray pressure was adjusted to 2 bar. The spray liquid A was then sprayed into the fluidized bed and the water was evaporated. In a further step, the spray liquid B was sprayed into the fluidized bed and the water was evaporated. The resulting granules were sieved through a sieve having a mesh width of 0.2 mm to remove any fine particles.

The table below illustrates the components used in the examples:

| Name | Chemical name | Source |
| --- | --- | --- |
| Tamol$^R$ NB | Naphthalenesulfonic acid/formaldehyde condensate | BASF AG |
| Ufoxane$^R$ 3A | Na ligninsulfonate | Borregaard |
| Morwet$^R$ D425 | Naphthalenesulfonic acid/formaldehyde condensate | BASF AG |
| Wettol$^R$ NT 1 | Alkylnaphthalene-sulfonate | BASF AG |
| Extrusil$^R$ | Finely divided calcium silicate | Degussa |
| Sipernat$^R$ 22 | Finely divided silica | Degussa |
| Anti-foam agent SRE | Silicone oil emulsion | Wacker-Chemie |
| Lutensol$^R$ ON 30 | Fatty alcohol ethoxylate (3EO) | BASF AG |
| Lutensol$^R$ ON 80 | Fatty alcohol ethoxylate (8EO) | BASF AG |
| Lutensol$^R$ GD 70 | Alkylpolyglycoside | BASF AG |
| AG$^R$ 6202 | 2-Ethylhexyl-glycoside | Akzo |
| Atplus$^R$ 450 | Alkylpolysaccharide/adjuvant blend | ICI |
| Agrimul$^R$ PG 2067 | $C_8$-$C_{10}$-Alkylpoly-glycoside | Henkel KGaA |
| Armoblem$^R$ 557 | Ethoxylated fatty amine | Akzo |
| Pluronic$^R$ PE 6400 | EO/PO block copolymer | BASF AG |
| Morwet$^R$ EFW | Anionic wetting agent blend | Witco |
| Sipernat$^R$ 50 S | Finely divided silica | Degussa |
| SU-1 | Comp. 47 from Table 1 | |
| Clefoxydim | 2-{1-[2-(4-Chlorophenoxy)propyloxyamino]butyl}-5-tetrahydrothiopyran-3-yl-cyclohexane-1,3-dione | |
| Cinidon-ethyl | Ethyl (Z)-2-chloro-3-[2-chloro-5-(4,5,6,7-tetrahydro-1,3-dioxoisoindoledion-2-yl)-phenyl]acrylate | |
| Aerosol OT B | Sodium dioctylsulfosuccinate/sodium benzoate mixture | Cyanamid |

TEST METHODS

The level of active SU in the formulations of the above examples was in each case determined by quantitative HPLC and is stated in percent in Table 3.

Tests on Storage Stability:

To examine the storage stability, samples of the respective formulations of Examples 1-18 and of the Comparative Examples 1 to 4 were stored for a specific time (14 d or 30 d) in tightly sealed glass vessels at the temperature stated in each case (54° C. or 50° C.). The samples were then examined and compared to the value before storage (zero value). The level of active compound is stated as the proportion of SU relation to the zero value (in percent). The storage tests were carried out similarly to the method CIPAC MT 46. In this method, the long-term storage stability of a product is estimated by short-term storage at elevated temperature.

Table 3 shows the results of the determination of the storage stability of the solid mixtures prepared in Examples 1-18 and Comparative Examples 1-4.

TABLE 3

| Ex. No. | Adjuvant | Level of active compound in % by weight | Relative level of active SU after 14 d, 54° C. | Relative level of active SU after 30 d, 50° C. |
| --- | --- | --- | --- | --- |
| C1 | Lutensol$^R$ ON 80 | 3.2 | 16 | — |
| C2 | Armoblem$^R$ 557 | 39 | 13 | — |
| C3 | Pluronic$^R$ PE 6400 | 10.4 | 39 | — |
| C4 | Lutensol$^R$ ON 30 | 7.3 | 48 | — |
| 1 | Lutensol$^R$ GD 70 | 5.6 | 87 | — |
| 2 | AG$^R$ 6202 | 6.3 | 86 | — |
| 3 | AG$^R$ 6202 | 5.9 | 95 | — |
| 4 | Atplus$^R$ 450 | 5.9 | 87 | — |
| 5 | Agrimul$^R$ PG 2067 | 5 | 78 | — |
| 6 | Lutensol$^R$ GD 70 | 5.15 | 92.2 | — |
| 7 | AG$^R$ 6202 | 5.49 | | 90 |
| 8 | AG$^R$ 6202 | 5.1 | 99 | — |
| 9 | Lutensol$^R$ GD 70 | 2.77 | | 98 |
| 10 | Lutensol$^R$ GD 70 | 2,77 | | 100 |
| 11 | AG$^R$ 6202 | 2.9 | 62 | — |
| 12 | AG$^R$ 6202 | 2.78 | 97.5 | — |
| 13 | AG$^R$ 6202 | 2.36 | 70 | — |
| 14 | AG$^R$ 6202 | | | — |
| 15 | AG$^R$ 6202 | 7.3 | 62 | — |
| 16 | Lutensol$^R$ GD 70 | 7.3 | 70 | — |
| 17 | AG$^R$ 6202 | 5.1 | — | — |
| 18 | AG$^R$ 6202 | 4.66 | 90 | — |

The results show the superior properties of the solid mixtures according to the invention.

We claim:

1. A solid mixture comprising
   a) a sulfonylurea herbicide,
   b) an alkylpolyglycoside, and
   c) optionally one or more further active compounds,
   with the proviso that said further active compound (c) is different from aminophosphoric acids.

2. The solid mixture as claimed in claim 1, comprising a sulfonylurea herbicide of the formula

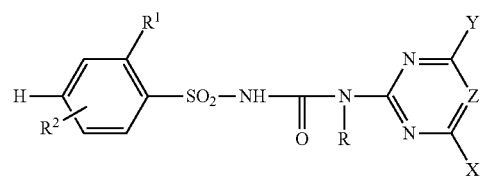

where:
R$^1$ is
  $C_1$-$C_4$-alkyl, which may carry from one to five of the following groups: methoxy, ethoxy, $SO_2CH_3$, cyano, chlorine, fluorine, $SCH_3$, and $S(O)CH_3$, halogen,
a group $ER^{19}$ in which E is O, S or $NR^{20}$,
$COOR^{12}$, $NO_2$, $S(O)_nR^{17}$, $SO_2NR^{15}R^{16}$ or $CONR^{13}R^{14}$;
$R^2$ is hydrogen, methyl, halogen, methoxy, nitro, cyano, trifluoromethyl, trifluoromethoxy, difluoromethoxy or methylthio;
Y is F, $CF_3$, $CF_2Cl$, $CF_2H$, $OCF_3$, $OCF_2Cl$, $C_1$-$C_4$-alkyl or $C_1$-$C_4$-alkoxy;
X is $C_1$-$C_2$-alkoxy, $C_1$-$C_2$-alkyl, $C_1$-$C_2$-alkylthio, $C_1$-$C_2$-alkylamino, di-$C_1$-$C_2$-alkylamino, halogen, $C_1$-$C_2$-haloalkyl, $C_1$-$C_2$-haloalkoxy;
R is hydrogen or methyl;
$R^{19}$ is $C_1$-$C_4$-alkyl, $C_2$-$C_4$-alkenyl, $C_2$-$C_4$-alkynyl or $C_3$-$C_6$-cycloalkyl, each of which may carry from 1 to 5 halogen atoms, furthermore, in the case that H is O or $NR^{20}$, $R^{19}$ is also methylsulfonyl, ethylsulfonyl, trifluoromethylsulfonyl, allylsulfonyl, propargylsulfonyl or dimethylsulfamoyl;
$R^{20}$ is hydrogen, methyl or ethyl;
$R^{12}$ is a $C_1$-$C_4$-alkyl group which may carry up to three of the following radicals: halogen, $C_1$-$C_4$-alkoxy, allyl or propargyl;
$R^{17}$ is a $C_1$-$C_4$-alkyl group which may carry from one to three of the following radicals: halogen, $C_1$-$C_4$-alkoxy, allyl or propargyl;
$R^{15}$ is hydrogen, a $C_1$-$C_2$-alkoxy group or a $C_1$-$C_4$-alkyl group;
$R^{16}$ is hydrogen or a $C_1$-$C_4$-alkyl group;
$R^{13}$ is H, $C_1$-$C_4$-alkyl, or $C_1$-$C_4$-alkoxy;
$R^{14}$ is $C_1$-$C_4$-alkyl;
n is 1-2; and
Z is N or CH.

3. The solid mixture as claimed in claim 1, comprising a further herbicidally active compound c).

4. The solid mixture as claimed in claim 1, comprising from 0.5 to 75% by weight of the component a).

5. The solid mixture as claimed in claim 1, comprising from 1 to 50% by weight of the component b).

6. The solid mixture as claimed in claim 1, comprising an alkylpolyglycoside having a degree of polymerization of 1-3.

7. The solid mixture as claimed in claim 6, comprising an alkylpolyglycoside having a degree of polymerization of 1-2.

8. A method of controlling undesirable plant growth, which comprises treating the plants and/or the area to be kept free of the plants with a herbicidal amount of a solid mixture as claimed in claim 1.

9. The solid mixture as claimed in claim 1, further comprising ammonium sulfate.

10. The method of claim 8, wherein the alkylpolyglycoside functions as a wetting agent.

11. The solid mixture as claimed in claim 1, wherein the sulfonylurea herbicide has the formula

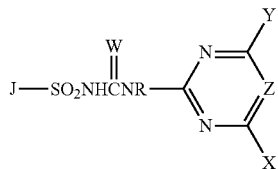

where
J is

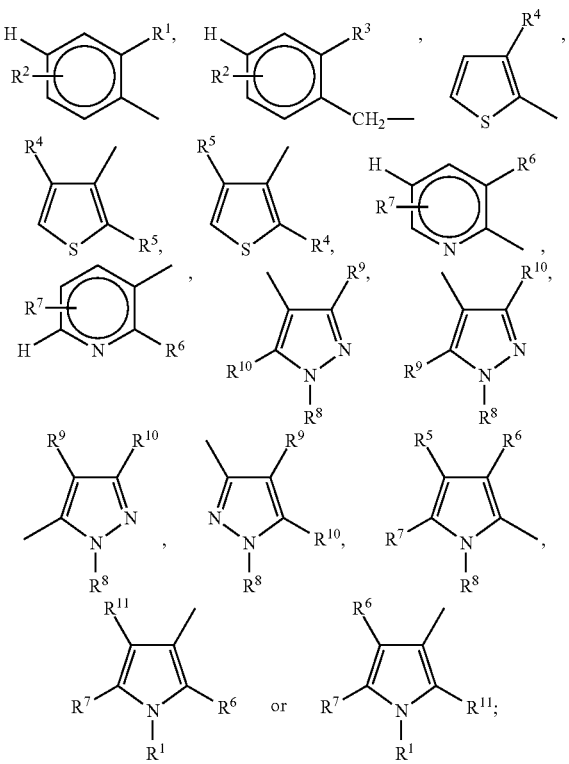

R is H or $CH_3$;
$R^1$ is F, Cl, Br, $NO_2$, $C_1$-$C_4$-alkyl, $C_1$-$C_4$-haloalkyl, $C_3$-$C_4$-cycloalkyl, $C_2$-$C_4$-haloalkenyl, $C_1$-$C_4$-alkoxy, $C_1$-$C_4$-haloalkoxy, $C_2$-$C_4$-alkoxyalkoxy, $CO_2R^{12}$, $C(O)NR^{13}R^{14}$, $SO_2NR^{15}R^{16}$, $S(O)_nR^{17}$, $C(O)R^{18}$, $CH_2CN$ or L;
$R^2$ is H, F, Cl, Br, CN, $CH_3$, $OCH_3$, $SCH_3$, $CF_3$ or $OCF_2H$;
$R^3$ is Cl, $NO_2$, $CO_2CH_3$, $CO_2CH_2CH_3$, $SO_2N(CH_3)_2$, $SO_2CH_3$, $SO_2CH_2CH_3$, $OCH_3$, or $OCH_2CH_3$;
$R^4$ is $C_1$-$C_3$-alkyl, $C_1$-$C_4$-alkoxy, $C_2$-$C_4$-haloalkenyl, F, Cl, Br, $NO_2$, $CO_2R^{12}$, $C(O)NR^{13}R^{14}$, $SO_2NR^{15}R^{16}$, $S(O)_nR^{17}$, $C(O)R^{18}$ or L;
$R^5$ is H, F, Cl, Br or $CH_3$;
$R^6$ is $C_1$-$C_4$-alkyl, $C_1$-$C_4$-alkoxy, $C_2$-$C_4$-haloalkenyl, F, Cl, Br, $CO_2R^{12}$, $C(O)NR^{13}R^{14}$, $SO_2NR^{16}R^{16}$, $S(O)_n R^{17}$, $C(O)R^{18}$ or L;
$R^7$ is H, F, Cl, $CH_3$ or $CF_3$;
$R^8$ is H, $C_1$-$C_4$-alkyl or pyridyl;
$R^9$ is $C_1$-$C_4$-alkyl, $C_1$-$C_4$-alkoxy, F, Cl, Br, $NO_2$, $CO_2R^{12}$, $SO_2NR^{16}R^{16}$, $S(O)_nR^{17}$, $OCF_2H$, $C(O)R^{18}$, $C_2$-$C_4$-haloalkenyl or L;
$R^{10}$ is H, Cl, F, Br, $C_1$-$C_4$-alkyl or $C_1$-$C_4$-alkoxy;
$R^{11}$ is H, $C_1$-$C_4$-alkyl, $C_1$-$C_4$-alkoxy, $C_2$-$C_4$-alkoxy; haloalkenyl, F, Cl, Br, $CO_2R^{12}$, $C(O)NR^{13}R^{14}$, $SO_2NR^{15}R^{16}$, $S(O)_nR^{17}$, $C(O)R^{18}$ or L;
$R^{12}$ is $C_1$-$C_4$-alkyl, with or without substitution by halogen, $C_1$-$C_4$-alkoxy or CN, allyl or propargyl;
$R^{13}$ is H, $C_1$-$C_4$-alkyl or $C_1$-$C_4$-alkoxy;
$R^{14}$ is $C_1$-$C_4$-alkyl;
$R^{15}$ is H, $C_1$-$C_4$-alkyl, $C_1$-$C_4$-alkoxy, allyl or cyclopropyl;
$R^{16}$ is H or $C_1$-$C_4$-alkyl;
$R^{17}$ is $C_1$-$C_4$-alkyl, $C_1$-$C_4$-haloalkyl, allyl or propargyl;

$R^{18}$ is $C_1$-$C_4$-alkyl, $C_1$-$C_4$-haloalkyl or $C_3$-$C_5$-cycloalkyl, with or without substitution by halogen;

n is 0, 1 or 2;

L has the structure

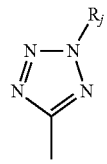

where $R_j$ is H or $C_1$-$C_3$-alkyl;

W is O or S;

X is H, $C_1$-$C_4$-alkyl, $C_1$-$C_4$-alkoxy, $C_1$-$C_4$-haloalkoxy, $C_1$-$C_4$-haloalkylthio, $C_1$-$C_4$-alkylthio, halogen, $C_2$-$C_5$-alkoxyalkyl, $C_2$-$C_5$-alkoxyalkoxy, amino, $C_1$-$C_3$-alkylamino or di($C_1$-$C_3$-alkyl)amino;

Y is H, $C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio, $C_2$-$C_5$-alkoxyalkyl, $C_2$-$C_5$-alkoxyalkoxy, amino, $C_1$-$C_3$-alkylamino, di($C_1$-$C_3$-alkyl)amino, $C_3$-$C_4$-alkenyloxy, $C_3$-$C_4$-alkanyloxy, $C_2$-$C_5$-alkylthioalkyl, $C_2$-$C_5$-alkylsulfinylalkyl, $C_2$-$C_5$-alkylsulfonylalkyl, $C_1$-$C_4$-haloalkyl, $C_2$-$C_4$-alkenyl, $C_3$-$C_5$-cycloalkyl, azido, fluorine or cyano; and Z is CH or N;

or is an agriculturally useful salt thereof.

12. The solid mixture as claimed in claim 1, wherein the alkylpolyglycoside has the formula

where $R^{21}$ is an alkyl radical having from 4 to 30 carbon atoms and Z is a glycoside radical having from 5 to 6 carbon atoms and a is in the range from 1 to 6.

13. The solid mixture as claimed in claim 1, wherein component (a) is present in from 0.5 to 75% by weight, and component (b) is present in from 1 to 50% by weight.

14. The solid mixture as claimed in claim 13, wherein component (a) is present in from 1 to 25% by weight, and/or component (b) is present in from 5 to 25% by weight.

15. The solid mixture as claimed in claim 13, wherein component (c) is present in from 1 to 60% by weight.

16. The solid mixture as claimed in claim 13, which further comprises, as component (d), from 0.5 to 25% by weight of one or more further surfactants.

17. The solid mixture as claimed in claim 13, which further comprises, as component (e), one or more customary formulation auxiliaries selected from the group consisting of: solid carriers, water-soluble compounds and salts, binders, lubricants, defoamers, and complex formers.

18. The solid mixture as claimed in claim 13, which is in form of granules having a mean particle size of from 200 μm to 2 mm.

19. The solid mixture as claimed in claim 1, which is in form of granules having a mean particle size of from 200 μm to 2 mm.

20. The solid mixture as claimed in claim 13, which consists essentially of a) from 1 to 25% by weight the sulfonylurea herbicide;

b) from 5 to 25% by weight of the alkylpolyglycoside;

and at least one component selected from the group consisting of:

c) from 1 to 60% by weight of the one or more further active compounds;

d) from 0.5 to 25% by weight of one or more further surfactants; and e) one or more customary formulation auxiliaries selected from the group consisting of: solid carriers, water-soluble compounds and salts, binders, lubricants, defoamers, and complex formers;

and which solid mixture is in form of granules having a mean particle size of from 200 μm to 2 mm.

* * * * *